(12) United States Patent
Zhai et al.

(10) Patent No.: US 11,505,834 B2
(45) Date of Patent: Nov. 22, 2022

(54) **METHOD FOR DETECTING *BRUCELLA* INFECTION AND APPLICATION THEREOF**

(71) Applicant: INNER MONGOLIA UNIVERSITY FOR THE NATIONALITIES, Inner Mongolia (CN)

(72) Inventors: Jingbo Zhai, Inner Mongolia (CN); Changlong Lv, Inner Mongolia (CN); Yongsheng Chen, Inner Mongolia (CN); Wei Gao, Inner Mongolia (CN); Leheng Zhao, Inner Mongolia (CN); Zeliang Chen, Inner Mongolia (CN)

(73) Assignee: INNER MONGOLIA UNIVERSITY FOR THE NATIONALITIES, Inner Mongolia (CN)

( * ) Notice: Subject to any disclaimer, the term of this patent is extended or adjusted under 35 U.S.C. 154(b) by 156 days.

(21) Appl. No.: 16/650,084

(22) PCT Filed: Nov. 30, 2017

(86) PCT No.: PCT/CN2017/113759
§ 371 (c)(1),
(2) Date: Mar. 24, 2020

(87) PCT Pub. No.: WO2019/075868
PCT Pub. Date: Apr. 25, 2019

(65) Prior Publication Data
US 2020/0232015 A1 Jul. 23, 2020

(30) Foreign Application Priority Data
Oct. 16, 2017 (CN) .......................... 201710961765.5

(51) Int. Cl.
*C12P 19/34* (2006.01)
*C12Q 1/689* (2018.01)
*C12N 15/10* (2006.01)

(52) U.S. Cl.
CPC ......... *C12Q 1/689* (2013.01); *C12N 15/1003* (2013.01); *C12Q 2527/125* (2013.01)

(58) Field of Classification Search
CPC .............................. C12Q 1/689; C12Q 1/6806
See application file for complete search history.

(56) References Cited

U.S. PATENT DOCUMENTS

2006/0147958 A1* 7/2006 Koshinsky ........... C12Q 1/6816
435/6.16

FOREIGN PATENT DOCUMENTS

| CN | 101368179 A | * | 2/2009 |
| CN | 101368179 A | | 2/2009 |
| CN | 106191286 A | | 12/2016 |

OTHER PUBLICATIONS

International Search Report (in English and Chinese) and Written Opinion published with PCT/CN2017/113759, dated Jul. 19, 2018, 9 pages provided.
Pang et al., "Changes of sTim-3 / HMGB1 and Spot forming cells of TGF-βsecreting from peripheral blood mononuclear cell in patients infected with *Brucella*", Chinese Journal of Immunology, vol. 33, Issue 2, Feb. 20, 2017, 5 pages provided; English Abstract is provided, Cited in ISR.

* cited by examiner

*Primary Examiner* — Kenneth R Horlick
(74) *Attorney, Agent, or Firm* — Hamre, Schumann, Mueller & Larson, P.C.

(57) ABSTRACT

The present invention provides a method for detecting *Brucella* infection, i.e., a serum and blood cell synchronous detection method. The detection method comprises two operation steps of serum sample detection and living blood cell sample detection and uses a supporting kit. The kit can be used for pretreatment of blood samples for clinically detecting *Brucella* in vitro. The serum and blood cell synchronous detection method can be used for early clinical rapid diagnosis of *Brucella* infection and medication guidance in the treatment process, and can also be used for prognosis, epidemiological survey of brucellosis, etc. The present invention can also be used for early clinical rapid diagnosis of other intracellular parasitic infection.

12 Claims, 1 Drawing Sheet

Specification includes a Sequence Listing.

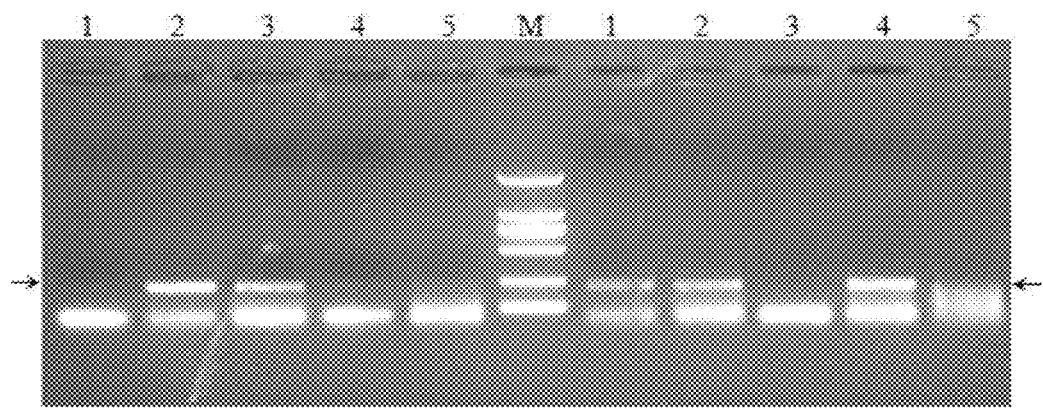

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
tggctcggtt gccaatatc                                        19

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
cgcttgcctt tcaggtctg                                        19

METHOD FOR DETECTING *BRUCELLA* INFECTION AND APPLICATION THEREOF

FIELD OF THE INVENTION

The present invention belongs to the fields of biochemistry and molecular biology, and particularly relates to a synchronous detection method for *Brucella* DNA in serum and blood cells and application thereof.

BACKGROUND OF THE INVENTION

The development and popularization of early rapid diagnosis technology for brucellosis (abbreviated as brucellosis) is one of the key technologies for effective prevention and control of brucellosis. The research, standardization and application of novel rapid diagnosis technology are the focus and difficulty of brucellosis research. The legal technical methods involved in the diagnosis of human and animal brucellosis in China include: plate agglutination test or rose-bengal plate agglutination test and whole milk ring test for primary screening, test tube agglutination test for serological test, complement fixation test and anti-human globulin test, as well as isolation of pathogenic bacteria. PCR can also be used for the brucellosis diagnosis for cows to detect pathogens. However, the isolation of pathogens takes a long time, is harsh in culture condition, complicated in technology and low in detection rate, and poses a great threat to the health and safety of experimenters. The traditional serological method has false positives and false negatives. With the development of science and technology, some new immunological and molecular biological brucellosis diagnosis technologies have been developed, such as enzyme-linked immunosorbent assay (ELISA), competitive ELISA, complement-binding ELISA, colloidal gold technology, fluorescence polarization test and various nucleic acid diagnosis technologies, most of which are based on the detection of *Brucella* antibodies in serum. The antibodies are produced several days after bacterial infection, and the antibodies cannot be detected from a considerable proportion of infected persons, so the treatment is delayed. Various nucleic acid diagnosis technologies are based on whole blood, and cannot determine whether the infecting *Brucella* is present in living cells. Therefore, although the above methods have their own characteristics, they all have certain limitations. It is necessary to comprehensively evaluate the sensitivity and specificity of these diagnosis technologies and their application values in the prevention, treatment and monitoring of brucellosis. The important problems to be solved urgently for *Brucella* infection include: early clinical rapid diagnosis of *Brucella* infection, medicinal efficacy and prognosis, specific detection of brucellosis epidemiology survey of *Brucella* in living cells, etc. So far, there is no independent method for the diagnosis of brucellosis, the diagnosis of brucellosis is mostly a combination of several methods, and the development of specific and sensitive diagnosis methods is still an urgent problem to be solved. In addition, before the large-scale promotion and application of various diagnosis technologies, it is necessary to prepare standardized diagnostic reagents and reference materials, and establish a corresponding standardized operation process.

The molecular biology technology represented by polymerase chain reaction (PCR) has become an important means for diagnosing brucellosis because of its high sensitivity and specificity. Since Fekete et al. first successfully reported the use of PCR to detect *Brucella*, it has become a hotspot of molecular biology in the study of brucellosis at home and abroad. Numerous PCR-derived methods have been developed for the direct identification of *Brucella*, and some of these technologies have been proved to be valuable for the diagnosis of human brucellosis. PCR technology can not only accurately identify *Brucella*, but also confirm and assist clinically in isolated culture and serum immunology methods, and is more advantageous than the traditional methods in patient follow-up and treatment monitoring. Experiments have shown that the PCR method is more sensitive than the serological method and bacterial culture. Because bacteria and bacterial debris appear in blood cells earlier than specific antibodies, the PCR method can give results within a short period of time when detecting brucellosis. Moreover, the PCR method is irrelevant to the bacterial infection pathway and the virulence of strains, so it has incomparable superiority in early diagnosis.

At present, PCR has been proved to be more sensitive than blood culture in acute and chronic diseases and more specific than serological tests, and can detect as little as 0.1 pg of DNA. In addition, the PCR technology can reduce the risk of laboratory-acquired *Brucella* infection caused by blood culture with high risk of infection. Moreover, *Brucella* DNA can be detected in different clinical specimens including serum, whole blood and urine samples, different tissues, cerebrospinal fluid, synovial fluid or pleural effusion, and pus, and the specimens are easy to obtain, so the PCR technology has become an important diagnosis method for laboratory detection of *Brucella*.

The pathogenesis of *Brucella* suggests that bacteria invade the body from the skin or mucous membranes, reach the lymph nodes with the lymph fluid, and are phagocytosed by phagocytic cells. If the phagocytic cells fail to kill the bacteria, the bacteria grow and multiply in the cells to form a local primary lesion. The proliferation of bacteria in the phagocytic cells causes phagocytic cells to rupture, and a large number of bacteria enter the lymphatic fluid and blood circulation to form bacteremia. In the blood, the bacteria are phagocytosed by mononuclear cells in the bloodstream and propagated therein, are carried along the bloodstream to the whole body, and multiply in the mononuclear-phagocytic system at the liver, spleen, lymph nodes, bone marrow, etc. to form multiple lesions.

The brucellosis is widespread in tissues and organs, but is common in the mononuclear-macrophage system, the osteoarticular system, the neurological system, etc. Therefore, blood samples are often used to diagnose human brucellosis. DNA extraction is the main reason that affects the wide application of PCR in the detection of *Brucella*. The main reason for the low sensitivity of PCR is the small amount of template DNA, so it is very important to optimize the DNA extraction method. The amounts of DNA extracted by the best DNA extraction kit and the poor DNA extraction kit differ by two orders of magnitude, so the amount of DNA extracted is largely related to the DNA purification kit. Any inhibition on the source of the DNA sample may limit the use of the PCR method. However, PCR inhibitors often interfere with the results. When the samples contain EDTA, RNASE, DNASE, heme, heparin, phenol, polyamines, plant polysaccharides, urine or calcium alginate, etc., or the samples are contaminated, false negative reactions may be caused.

PCR detection of *Brucella* DNA is also subject to various factors such as the acute, subacute or chronic phase of sample collection, as well as the method of extracting template DNA and mutual contamination between templates. *Brucella* PCR mainly uses DNA nucleic acid extracted from the sample as a template, so nucleic acid extraction is an indispensable step in PCR detection. Past studies have shown that the efficiency of nucleic acid extraction by different kits is different, and affects the detection lower limit of fluorescent quantitative PCR, and the maximum difference of detection lower limits can reach 500 times. It can be seen that the efficiency of nucleic acid extraction (including DNA amount and DNA purity) has a great impact on PCR sensitivity. Exploring more efficient nucleic acid extraction methods has become an effective means to improve the sensitivity of PCR detection and then increase the detection rate of brucellosis.

SUMMARY OF THE INVENTION

The technical problem to be solved by the present invention is to provide a new method for detecting *Brucella* infection, which can synchronously detect *Brucella* DNA in serum and blood cells. The present invention provides a pretreatment kit for blood cell sample detection for detecting *Brucella* infection and an application thereof.

Specifically, in a first aspect, the present invention provides a pretreatment kit for a blood cell sample for detecting *Brucella* infection, comprising containers filled with Solution I, Solution II, Solution III, Solution III, Solution IV and Solution V respectively, wherein Solution I is an aqueous solution containing 368 mg/42 mL of sodium chloride;

Solution II is an aqueous solution containing 1 g/125 mL of sodium chloride, 25 mg/125 mL of potassium chloride, 177.5 mg/125 mL of disodium hydrogen phosphate and 33.75 mg/125 mL of potassium dihydrogen phosphate;

Solution III is an aqueous solution containing 42.399 mg/35 mL of trihydroxymethyl aminomethane, 306.81 mg/35 mL of sodium chloride and 102.284 mg/35 mL of ethylenediamine tetraacetic acid;

Solution IV is TRITON™ X-100 or an aqueous solution containing 35 mg/0.35 mL of sodium dodecyl sulfate;

Solution V is double distilled water.

Preferably, the pH value of Solution III can be adjusted to pH 8.0 (25° C.).

In a second aspect, the present invention provides an application of the kit according to the first aspect of the present invention in preparation of a reagent product for a method for detecting *Brucella* infection, wherein the kit detects serum *Brucella* DNA and blood cell *Brucella* DNA, i.e., the kit can be used for simultaneous detection of *Brucella* DNA in serum and blood cells.

Preferably, in the application of the second aspect of the present invention, the kit is used for enriching living cells infected by *Brucella* in peripheral blood, and isolating and extracting *Brucella* DNA.

Preferably, in the application of the second aspect of the present invention, the method for detecting *Brucella* infection determines whether *Brucella* DNA is present in living blood cells by extracting DNA from the living cells, and then determines whether the test object is infected.

Preferably, in the application of the second aspect of the present invention, the method for detecting *Brucella* infection is used for detecting *Brucella* DNA of living cells infected in body fluid.

Preferably, in the application of the second aspect of the present invention, the method for detecting *Brucella* infection is capable of detecting *Mycobacterium tuberculosis* infection or other intracellular parasitic infection.

Preferably, in the application of the second aspect of the present invention, the serum and the blood cells are serum and living blood cells in the same peripheral blood taken from the same *Brucella* infected person. More preferably, the blood cells are living monocytes in the peripheral blood.

Preferably, in the application of the second aspect of the present invention, the detection of serum *Brucella* DNA comprises the following operation steps:

taking 0.2 mL of serum into a 1.5 mL Ep tube; centrifuging at room temperature, 15000×g for 15 minutes; discarding the supernatant; adding 0.2 mL of Solution V to the 1.5 mL Ep tube; shaking; centrifuging at room temperature, 15000×g for 10 minutes; discarding the supernatant; adding 20 μL of Solution V to the 1.5 mL Ep tube; shaking, and instantaneously centrifuging; heating at 100° C. for 10 minutes; placing in ice or in a −20° C. refrigerator for 2 minutes; centrifuging at room temperature, 15000×g for 10 seconds; and sucking 15 or 10 μL of supernatant as a template for PCR (including fluorescent quantitative PCR).

The Ep tube is an abbreviation of an Eppendorf tube, which is commonly used by the person skilled in the art.

Preferably, in the application of the second aspect of the present invention, the detection of blood cell *Brucella* DNA comprises the following operation steps:

taking 1 mL of peripheral blood; adding 1 mL of Solution I and mixing uniformly; spreading on a 6-well cell culture plate; incubating at 37° C. for 1 hour; discarding the supernatant, and washing with Solution II until no red; adding 1 mL of Solution II to wells of the cell culture plate, repeatedly blowing, and washing away the sediment (i.e., living monocytes) at the bottom of the wells to a 1.5 mL Ep tube; centrifuging at 4° C., 500×g for 5 minutes; discarding the supernatant; adding 800 μL of Solution III, and mixing thoroughly; adding 8 μL of Solution IV, and mixing thoroughly; incubating at 55° C. for 1 hour; centrifuging at room temperature, 8000 rpm for 10 minutes; discarding the supernatant; adding 800 μL of Solution V, and mixing thoroughly; centrifuging at room temperature, 8000 rpm for 10 minutes; discarding the supernatant; adding 20 L of Solution V, shaking, and mixing thoroughly; heating at 100° C. for 10 minutes; centrifuging at room temperature, 15000×g for 10 seconds; sucking 15 or 10 μL of supernatant as a template for PCR (including fluorescent quantitative PCR).

More preferably, in the application of the second aspect of the present invention, the operation step of detecting blood cell *Brucella* DNA can release *Brucella* contained in living blood cells.

In a third aspect, the present invention provides an application of the kit according to the first aspect of the present invention in preparation of a reagent product for early clinical rapid diagnosis of *Brucella* infection.

In a fourth aspect, the present invention provides an application of the kit according to the first aspect of the present invention in preparation of a reagent product for medication guidance and medicinal efficacy determination in the treatment of brucellosis.

In a fifth aspect, the present invention provides an application of the kit according to the first aspect of the present invention in preparation of a reagent product for prognosis of brucellosis.

In a sixth aspect, the present invention provides an application of the kit according to the first aspect of the present invention in preparation of a reagent product for epidemiological survey of brucellosis.

In a seventh aspect, the present invention provides an application of the kit according to the first aspect of the present invention in preparation of a tool for scientific research on *Brucella*.

In an eighth aspect, the present invention provides an application of the kit according to the first aspect of the present invention in preparation of a reagent product for physical examination of pastoral farmers.

In order to promote the application of the PCR method in the clinical diagnosis of brucellosis, the patent has invented a method for detecting *Brucella* infection, that is, a serum and blood cell synchronous detection method. The detection method comprises two operation steps of serum sample detection and blood cell (mainly referring to living monocyte) sample detection and uses a supporting kit. The blood cell detection has the following advantages over whole blood detection:

1. The characteristics of adherent growth of fresh (generally within 3 hours after blood collection) monocytes on a solid (glass or polystyrene) culture dish (or culture plate) is fully utilized, red blood cells accounting for about 45% of the whole blood are washed out, and the monocytes are purified and concentrated, thereby ensuring the minimum amount of DNA template and the purity required for the PCR (PCR inhibitors such as hemoglobin can be thoroughly removed before cell disruption).

2. The collected monocytes are fully suspended in the buffer solution of the kit, and then the surfactant is added to lyse cell membranes to ensure that each cell can be fully lysed and release *Brucella* as much as possible. The inventors have found by repeated experiments that if the surfactant is prepared into a buffer solution to lyse monocytes and perform PCR by the same steps as described in the methods of a lot of existing literature, *Brucella* DNA cannot be detected. The reason is that after the monocyte mass is added to the buffer solution containing the surfactant, before the cells are not fully suspended, a layer of cells outside the cell mass has been lysed, and the lysed cells release a viscous substance to tightly wrap the cell mass and block further contact between the buffer solution and the cells inside the cell mass, so that the surfactant cannot lyse more cell membranes, and the intracellular bacteria cannot be released.

3. The main principle of lysing cell membranes by surfactants is to dissolve membrane proteins in the cell membranes. The surfactants include nonionic surfactants, anionic surfactants and amphoteric surfactants. The nonionic surfactant TRITON™ X-100 is used as a cell membrane lysing agent in the present invention, mainly considering subsequent PCR, where low concentration TRITON™ X-100 does not affect PCR, 0.01% TRITON™ X-100 promotes PCR, and high concentration TRITON™ X-100 is a PCR inhibitor. The inventors have found by repeated experiments that 1% TRITON™ X-100 is just right for the lysis of cell membranes, not only ensures sufficient lysis of cell membranes, but also ensures that the electrophoresis bands of the subsequent PCR product are clear, which can be clarified by the phenomenon that the solution becomes clear from cloudy after the addition of the surfactant. If cell membranes are lysed with TRITON™ X-100 having the concentration of 2% or more, although the cell membranes are lysed more thoroughly, the electrophoresis bands of the subsequent PCR product are blurred. If the anionic surfactant SDS (sodium dodecyl sulfate) is used as a lysing agent, the residual SDS can be removed as much as possible by multiple times of cleaning in the cleaning phase only at a very low concentration (e.g., 0.1%) so as to ensure the subsequent PCR, but the amount of DNA template recovered is reduced. SDS is a PCR inhibitor, so it is not preferred as a lysing agent.

4. If the whole blood is taken as a sample for DNA extraction, the positive result of PCR cannot prove that the *Brucella* DNA in the serum or in the blood cells is amplified, and cannot determine that the serum or the blood cells are positive. If the PCR result is positive, the blood cell sample detection of the present invention can definitely determine that the blood cells are infected with *Brucella*, which is unmatched by the whole blood as a sample for DNA extraction and PCR.

5. The blood cell sample detection is more sensitive than whole blood sample detection in PCR, because the DNA extracted by the kit provided by the present invention is more advantageous than the DNA extracted by the commercial conventional blood genome extraction kit or bacterial genome extraction kit in two aspects: the minimum amount of DNA template for PCR positive reaction can be ensured, and the purity of the extracted DNA is high. For the amount of DNA template, the blood cell sample of the present invention is 1 mL of peripheral blood. The isolation, extraction, concentration and full recovery of DNA by the kit of the present invention as a template for PCR ensure the minimum amount of DNA template for PCR positive reaction. The amount of the whole blood sample treated by the commercially available DNA extraction kit is generally not more than 0.2 mL. Otherwise, the subsequent operation is very troublesome. Even if 1 mL peripheral blood is intentionally treated, the DNA is greatly reduced after the subsequent cumbersome purification treatment, and infecting *Brucella* cannot be detected by PCR in many cases, which explains the low positive rate of PCR detection in clinical whole blood samples. To take a step back, even if infecting *Brucella* DNA can be detected from individual patients, the cumbersome purification operation limits the universal application of this method to clinical diagnosis. For DNA purity, the DNA extracted by the kit of the present invention is not exposed to PCR inhibitors such as hemoglobin from the start to the end, and the extracted DNA is isolated from the red blood cells containing PCR inhibitors such as hemoglobin and other cells through the living monocytes adherent culture at the beginning of the blood cell sample detection, so the extracted DNA is highly purified. When the whole blood sample is treated with the current commercial DNA extraction kit, the PCR inhibitors such as hemoglobin contained in the red blood cells are mixed with the extracted DNA, so the subsequent phenol treatment (phenol:chloroform:isoamµL alcohol is 25:24:1) inevitably affects the purity of the subsequent reaction template DNA. Considering that the residual phenol affects subsequent PCR, the extracted DNA is not treated with phenol, but subjected to other complicated operations such as multiple times of cleaning, so the purity required by the PCR template is still not achieved.

Even if the world's best QIAamp® UCP Pathogen Kits for DNA extraction from Qiagen are used to efficiently lyse and purify pathogenic nucleic acids in whole blood samples (see Qiagen's product description: QIAGEN provides QIAamp UCP Pathogen Kits for reliable purification of nucleic acids from whole blood or DNA from a variety of sample types.), or multiple types of sample pathogenic DNA, and the QIAGEN kits have the characteristic of efficient lysis (Efficient lysis of microbial cells) and lyse pathogenic bacteria contained in the whole blood by the mechanical bead grinding principle (These tubes provide efficient lysis of microbial cells with a mechanical bead beating step.), eukaryotic cells such as red blood cells are inevitably ground and lysed while the pathogenic bacteria are lysed by mechanical bead grinding. Obviously, when the pathogenic bacteria DNA is released, the eukaryotic genomic DNA or hemoglobin and the like are also released, and mixed with the target DNA to be detected. The QIAGEN kit also has the characteristic of efficient purification (Efficient purification of nucleic acids), that is, purify the pathogenic bacteria DNA while digesting the eukaryotic DNA (The QIAamp UCP PurePathogen Blood Kit enables purification of bacterial, fungal, viral, and free-circulating nucleic acids by parallel depletion of human DNA.). Thus, it can be seen that the process of extracting and purifying pathogenic bacteria DNA in whole blood by the Qiagen's DNA extraction kit is first lysis and then purification (Contaminants are washed away during 3 wash steps for inhibitor-free purification.). However, the "serum and blood cell synchronous detection" of the present invention is different, and the process of extracting and purifying the pathogenic bacteria DNA in the serum or blood cells is first purification and then lysis, as described in detail above. In theory, the "serum and blood cell synchronous detection" method is more thorough in extraction and purification of the pathogenic bacteria DNA (because the red blood cells containing impurities are isolated in advance to reduce mixing of hybrid nucleic acids, hybrid proteins and the like with the target DNA).

6. The serum and blood cell synchronous detection is more comprehensive than single serum sample detection or whole blood sample detection. For patients with early infection, acute infection or bacteremia, the positive rate of the serum sample detection is high. For patients in the treatment period or chronic patients, due to the combined use of antibiotics, the bacteria in the serum are killed and cleared, and the *Brucella* hidden in the monocytes cannot be cleared, so the whole blood sample fails in PCR detection. In contrast, the *Brucella* can be easily detected in a blood cell sample by PCR in the present invention. This conclusion can be drawn from Embodiment 4. In other words, for the three cases where the *Brucella* is contained in only serum, in only blood cells and in both serum and blood cells, the *Brucella* can be clearly diagnosed by the serum and blood cell synchronous detection method of the present invention. This cannot be achieved by single serum sample PCR detection or single whole blood sample PCR detection.

Even with Qiagen's products, it is impossible to determine where the pathogenic bacteria are located, that is, in serum or in blood cells or in both serum and blood cells. The "serum and blood cell synchronous detection" of the present invention can determine the location of *Brucella*, that is, in single serum, in single blood cells, or in both serum and blood cells. The determination of the location of *Brucella* is of great significance in clinical diagnosis and treatment.

7. The blood cell sample PCR detection provided by the present invention includes ordinary PCR, fluorescent quantitative PCR and various other derived PCRs. The ordinary PCR requires agarose gel electrophoresis, and has a semi-quantitative effect on intracellular *Brucella* DNA. The fluorescent quantitative PCR can directly quantify *Brucella* DNA without electrophoresis. Although the PCR after whole blood samples are treated with commercially available genomic DNA extraction kits can also semi-quantify or quantify *Brucella* DNA, but the results are not objective, which means that the detection results of different persons are not comparable, because the kits used vary widely, the abilities of different kits to extract and purify pathogenic bacteria are different, and the detection results are also different. This is the root cause of the fact that the whole blood sample PCR detection cannot be widely used in clinical diagnosis of brucellosis. Of course, the serum sample PCR detection can also semi-quantify or quantify *Brucella* DNA. However, the serum sample PCR detection has not been widely used in clinical diagnosis of brucellosis, mainly based on the fact that it cannot objectively reflect all clinical *Brucella* infections.

8. For a certain number of chronic or recurrent brucellosis patients who are clinically cured and do not have any symptoms, the *Brucella* DNA load can still be detected months or even years later. Therefore, the clinical response of brucellosis patients to antibiotic treatment is not equivalent to the gradual elimination of pathogenic bacteria. Some clinically cured patients carry low-level *Brucella* DNA, which may be related with *Brucella* in human monocyte-macrophages for a long time and in low-level proliferation. This is one of the common causes of recurrence in brucellosis patients. The serum and blood cell synchronous detection of the present invention is a relatively effective method for identifying chronic brucellosis patients, and is especially suitable for the patients who have symptoms and no complications and cannot be identified by the existing test methods.

The serum and blood cell synchronous detection method of the present invention has the following characteristics for clinical diagnosis of *Brucella* infection:

1. The "serum and blood cell synchronous detection" can clarify whether *Brucella* DNA is present in living blood cells (specifically, living monocytes). The extraction of DNA from living cells can indicate that the test object is currently in an infected state, which is more exact than the diagnostic information obtained by conventional clinical detection of antibodies in serum. The positive antibodies can only indicate that the test object has been infected or is in the infection period, but cannot determine the state of being infected. *Brucella* DNA usually cannot be detected from the serum of a chronic brucellosis patient in treatment, for the *Brucella* hidden in living cells cannot be killed by antibiotics and other drugs. *Brucella* DNA cannot be detected from the serum of the chronic patient, but if *Brucella* DNA is detected in living blood cells, it indicates that the patient is still infected. The above clinical diagnostic information cannot be clearly acquired if the same patient is detected with Qiagen's DNA extraction kit. For example, after a patient was treated, the pathogenic bacteria have been cleared from the living blood cells, but *Brucella* may still remain in the blood, and in this case, if Qiagen's DNA extraction kit is used, *Brucella* DNA may be extracted and tested. Instead, the "serum and blood cell synchronous detection" method cannot detect *Brucella* DNA. Thus, the clinical diagnosis results are very different. The scientific natures of the two methods in clinical diagnosis are self-evident, and the "serum and blood cell synchronous detection" method is closer to the clinical objective results.

2. The pathogenic bacteria nucleic acid detection for *Brucella* DNA is high in operation safety. At present, the target for clinical diagnosis mainly includes isolated culture of pathogenic bacteria, but the method is technically demanding, time-consuming, laborious and low in positive rate, and poses a great threat to the safety of operators. Many serological antibody detection methods cannot be used alone for clinical diagnosis, should be combined for use, and diagnose false negatives and false positives in diagnosis. Meanwhile, the serological detection methods may cross-react with a variety of microorganisms, and sometimes it is difficult to distinguish that the lower-titer serological detection result is of *Brucella* infection or cross reaction. Complement fixation test (CFT) and anti-human immunoglobulin test (Coomb's) are cumbersome in operation and small in range of use. Fluorescence polarization test (FPA) and colloidal gold immune-chromatographic assay (GICA) cannot distinguish the serological reactions induced by natural infection and vaccine immunization, so false positives and false negatives are prone to occur, and FPA and GICA have not been widely used.

3. The sensitivity of extracting *Brucella* DNA in peripheral blood is high. 10 pg of DNA can be detected by ordinary PCR, and 0.1 pg of DNA can be detected by fluorescent quantitative PCR.

4. The accuracy is high in subsequent clinical diagnosis, and nearly no missed detection is achieved (the missed detection rates of the traditional clinical diagnosis methods RBPT, SAT, PAT, AGT, ELISA, colloidal gold and the like are about 37%).

5. The present invention can be used for early rapid diagnosis (*Brucella* can be detected out before specific antibodies are produced), so that the clinical diagnosis is windowless.

6. The distribution information of bacteria in serum and blood cells can be provided for clinic, and the degree of infection can be quantitatively determined.

7. The present invention can be used for medication guidance and medicinal efficacy judgment in the treatment of brucellosis.

8. The present invention can be used as a judgment indicator of recovery or clinical cure.

9. The combination of the *Brucella* DNA extracted by the kit of the present invention and the probe fluorescent quantitative PCR (Cycling Probe method) can identify natural infection and vaccination infection by using single nucleotide polymorphism (SNP) sites.

10. The present invention can provide a more sensitive and accurate new technology for epidemiological survey of brucellosis.

The serum and blood cell synchronous detection method of the present invention overcomes the deficiencies of false negative and the like to a great extent in PCR detection with the template treated by the existing DNA extraction kit. The PCR technology can be more widely applied to clinical diagnosis, has a broad application prospect in monitoring of illness of brucellosis patients, prognosis, medication guidance and the like, and also provides a powerful tool for scientific research of *Brucella*. Therefore, the serum and blood cell synchronous detection technology of the present invention will open up a new field for the clinical diagnosis of brucellosis, and can become a clinical diagnosis method for brucellosis.

For ease of understanding, the present invention will be described in detail below through specific embodiments. It should be noted that the descriptions are only illustrative, and are not intended to limit the scope of the present invention. Many variations and modifications made to the present invention are apparent to the person skilled in the art according to the description.

BRIEF DESCRIPTION OF THE DRAWING

FIG. 1 shows a nucleic acid electrophoretogram of serum and blood cell PCR detection of *Brucella* infected patients, wherein 1, 2, 3, 4, 5 are five clinical patients, the left side is a serum *Brucella* DNA PCR detection map, and the right side is a corresponding blood cell *Brucella* DNA PCR detection map of the same patients; M is Marker; 1.5% agarose gel, 5 µL sample loading quantity; left and right arrows refer to target DNA bands.

DETAILED DESCRIPTION OF EMBODIMENTS

The chemical reagents used in the following experimental operations were purchased from Sinopharm Chemical Reagent Co., Ltd., and the PCR kit and the agarose gel were purchased from Takara. All experiments were performed as usual in molecular biology experiments.

Embodiment 1 Kit Components (Based on the Amount for a Kit to Detect 40 *Brucella* Infected Persons)

Solution I (42 mL): 368 mg of sodium chloride; Solution II (125 mL): 1 g of sodium chloride, 25 mg of potassium chloride, 177.5 mg of disodium hydrogen phosphate, and 33.75 mg of potassium dihydrogen phosphate; Solution III (35 mL): 42.399 mg of trihydroxymethyl aminomethane, 306.81 mg of sodium chloride, and 102.284 mg of ethylenediamine tetraacetic acid, 25° C. pH 8.0; Solution IV (0.35 mL): TRITON™ X-100; Solution V (45 mL):double distilled water.

Embodiment 2 Serum Sample Detection Steps

Take 0.2 mL of serum into a 1.5 mL Ep tube; centrifuge at room temperature, 15000×g for 15 minutes; add 0.2 mL of Solution V to the 1.5 mL Ep tube; shake; centrifuge at room temperature, 15000×g for 10 minutes; discard the supernatant; add 20 µL of Solution V to the 1.5 mL Ep tube; shake, and instantaneously centrifuge; heat at 100° C. for 10 minutes; place in ice or in a −20° C. refrigerator for 2 minutes; centrifuge at room temperature, 15000×g for 10 minutes; and suck 15 (10) µL of supernatant as a template for PCR (including fluorescent quantitative PCR).

Embodiment 3 Blood Cell Sample Detection Steps

Take 1 mL of peripheral blood; add 1 mL of Solution I and mix uniformly; spread on a 6-well cell culture plate; incubate at 37° C. for 1 hour; wash with Solution II thoroughly (no red), and discard the supernatant; add 1 mL of Solution II to holes of the cell culture plate, repeatedly blow, and wash away the sediment (monocytes) at the bottom of the wells to a 1.5 mL Ep tube; centrifuge at 4° C., 500×g (about 1000 rpm) for 5 minutes; discard the supernatant; add 800 µL of Solution III, and mix thoroughly; add 8 µL of Solution IV, and mix thoroughly; incubate at 55° C. for 1 hour; centrifuge at room temperature, 8000 rpm for 10 minutes; discard the supernatant; add 800 µL of Solution V, and mix thoroughly; centrifuge at room temperature, 8000 rpm for 10 minutes; discard the supernatant; add 20 µL of Solution V, shake, and mix thoroughly; heat at 100° C. for 10 minutes; centrifuge at room temperature, 15000×g for 10 seconds; suck 15 (10) L of supernatant as a template for PCR (including fluorescent quantitative PCR).

Embodiment 4 PCR Detection Results of a Small Amount of Samples Using the Above Reagents and Methods Serum and blood cell samples were collected from outpatients at Tongliao Endemic Disease Prevention and Treatment Stations from 8 Dec. 2016 to 5 Jan. 2017. The two kinds of samples were respectively subjected to the serum sample detection and blood cell sample detection steps of the present invention, and *Brucella* genomic DNA was extracted by using the kit of the present invention as a PCR template for PCR.

Taking BCSP31 as a target gene, the primer sequences include B4 having the sequence of TGGCTCGGTTGC-CAATATC (SEQ ID NO.: 1) and B5 having the sequence of CGCTTGCCTTTCAGGTCTG (SEQ ID NO.: 2).

PCR system: B4 (20 µmol/L), 0.5 µL; B5 (20 µmol/L), 0.5 µL; dNTP Mixture (2.5 mmol/L each), 2 µL; 10×Buffer ($Mg^{2+}$ plus), 2.5 µL; Taq DNA Polymerase (5 U/µL), 0.125 µL; template DNA, 15 µL or 10 µL of DNA extracted using the kit of the present invention; add the balance of double distilled water to 25 µL.

PCR condition: DNA pre-denaturation at 90° C. for 5 minutes; denaturation at 90° C. for 1 minute, annealing at 53° C. for 1 minute, 72° C. extension for 1 minute, 40 cycles; 72° C. for 10 minutes; 4° C. cooling.

FIG. 1 shows a nucleic acid electrophoretogram of serum and blood cell PCR detection of *Brucella* infected patients. It can be seen from the nucleic acid electrophoretogram of PCR detection that all 5 patients were infected with *Brucella*. By detection, patient 1 had negative serum and strongly positive blood cells; patient 2 had strongly positive serum and blood cells; patient 3 had strongly positive serum and negative blood cells; patient 4 had positive serum and blood cells, but the serum was extremely weak positive, it can be determined that the patient's serum contained trace *Brucella*, that is, the bacterial load of the serum was very low, the blood cells were strongly positive, it can be determined that the bacterial load of the patient's blood cells was high, and the patient can be diagnosed as a chronic brucellosis patient in a treatment phase in combination with the patient's other clinical manifestations; the conclusion of patient 5 was the same as that of patient 4, but from the position of the DNA band indicated by the right arrow, it can be seen that the *Brucella* load of the blood cells of patient 5 may be higher, the infected bacteria type may also be different from that of other patients, and further genetic identification is needed.

Embodiment 5 Analysis on the Results of Serum and Blood Cell Synchronous Detection of 300 Brucellosis Patients Using the Above Reagents and Method, and the Results of Rose-Bengal Plate Agglutination and Tube Agglutination Test 1. Samples were collected from 8 Dec. 2016 to 26 May 2017, in a total of 300 people including clinic suspected cases in hospitals of Tongliao City and people who had a history of exposure to *Brucella* and volunteered to receive brucellosis antibody detection and physical examination in Tongliao Endemic Disease Prevention and Treatment Stations.

2. Detection reagents, including brucellosis rose-bengal plate agglutination antigen reagent, brucellosis tube agglutination antigen reagent, and positive serum and negative serum of brucellosis, were purchased from the National Institute for Communicable Disease Control and Prevention, and were all within the validity period.

3. Samples were collected using blood collection tubes with a separation gel coagulant, 5 mL of whole blood of test objects was taken on seat, the whole blood was centrifuged after 30 minutes to separate serum, and the serum was stored at 4° C. for later use.

4. Materials and methods required for serum and blood cell synchronous detection are the same as those in Embodiment 4.

5. SAT test was operated according to the daily standard operating procedures, the serum to be tested was diluted with 0.5% carbolic acid normal saline, 0.5 mL of liquid was reserved in each tube, then 0.5 mL of 10 times diluted brucellosis tube agglutination antigen reagent was added, and the final serum dilution was 1:25, 1:50, 1:100, 1:200. The same method was used to make negative and positive control tubes and turbidimetric tubes. After fully shaking, the serum was incubated in a 37° C. incubator for 20 to 22 hours, then taken out, and placed at room temperature for 2 hours to observe the results.

6. RBPT test was operated according to the daily standard operating procedures, 30 µL of serum to be tested was sucked onto a clean glass slide with a pipette, the tip was discarded and replaced with a new one to suck 30 µL of rose-bengal plate agglutination antigen reagent to mix thoroughly with the serum, and results were observed within 5 minutes.

7. The results were judged according to the 2007 edition of WS269-2007 Brucellosis Diagnosis Criteria issued by the Ministry of Health of the People's Republic of China. SAT recorded serum dilution and transparency in the form of (−), 1:25 (+), 1:25 (++) . . . 1:200 (++++); RBPT recorded the degree of agglutination in the form of (−), (+−), (+), (++), (+++) and (++++). The results of contrast analysis were shown in Table 1, and the test results of 300 cases were shown in Table 2.

TABLE 1

Contrast analysis results of 300 cases

| | | |
|---|---|---|
| Blood cell PCR (+) 225 cases (75%) | Antibody (+) 167 cases (55.7%) Antibody (−) 58 cases (19.3%) | Confirm 279 cases of brucellosis (93%) |
| Serum PCR (+) 153 cases (51%) | Antibody (+) 130 cases (43.3%) Antibody (−) 23 cases (7.7%) | |
| Blood cell and serum simultaneous PCR (+) 99 cases (33%) | Antibody (+) 93 cases (31%) Antibody (−) 6 cases (2%) | |
| Blood cell PCR (+) or serum PCR (+) 279 cases (93%) | Antibody (+) 204 cases (68%) Antibody (−) 75 cases (25%) | |
| Blood cell and serum simultaneous PCR (−) 21 cases (7%) | Antibody (+) 20 cases (6.7%) Antibody (−) 1 case (0.3%) | Exclude 21 cases of brucellosis (7%) |

Conclusion:

In serum and blood cell synchronous detection, brucellosis confirmation rate 279/300=93%, brucellosis exclusion rate 21/300=7%.

In antibody test, brucellosis confirmation rate 174/300=58%.

TABLE 2

Test results of 300 cases

| Date | No. | Gender | Age | Address | PCR Blood Cells | PCR Serum | Clinic Result SAT | Clinic Result RBPT |
|---|---|---|---|---|---|---|---|---|
| December 8 | 1 | male | 34 | Kequ | + | + | − | − |
| December 9 | 2 | male | 35 | Zuozhong | + | + | 1:25++ | + |
| | 3 | male | 43 | Houqi | + | + | 1:200++++ | + |

TABLE 2-continued

Test results of 300 cases

| Date | No. | Gender | Age | Address | PCR Blood Cells | PCR Serum | Clinic Result SAT | Clinic Result RBPT |
|---|---|---|---|---|---|---|---|---|
| | 4 | male | 24 | Kequ | − | + | − | − |
| | 5 | male | 48 | Houqi | + | + | 1:100++++ | + |
| | 6 | female | 37 | Kequ | + | − | 1:200++++ | + |
| December 19 | 7 | male | 71 | Kequ | + | − | 1:200++ | + |
| | 8 | male | 34 | Houqi | + | − | 1:200++ | + |
| | 9 | male | 39 | Houqi | + | − | − | − |
| | 10 | female | 29 | Zuozhong | + | − | − | − |
| | 11 | male | 40 | Heilongjiang | + | − | 1:25++ | + |
| | 12 | male | 20 | Heilongjiang | + | − | 1:50++ | + |
| | 13 | female | 40 | Heilongjiang | + | + | − | − |
| | 14 | male | 46 | Kequ | − | − | 1:25++ | + |
| | 15 | female | 32 | Development District | + | − | − | − |
| | 16 | female | 53 | Zuozhong | + | − | 1:200++ | + |
| | 17 | female | 46 | Zuozhong | + | − | 1:50++ | + |
| | 18 | male | 26 | Liaoning | + | − | − | − |
| | 19 | female | 44 | Heilongjiang | − | − | 1:50++ | + |
| | 20 | male | 42 | Heilongjiang | + | − | 1:50++ | + |
| | 21 | male | 59 | Kailu | + | − | 1:200++ | + |
| December 21 | 22 | male | 60 | Houqi | + | − | 1:50++ | + |
| | 23 | female | 23 | Houqi | + | − | 1:200++++ | + |
| | 24 | male | 34 | Houqi | + | − | − | + |
| | 25 | female | 44 | Zuozhong | + | − | 1:50++ | + |
| December 26 | 26 | male | 57 | Kequ | + | − | − | − |
| | 27 | female | 57 | Youzhong | + | − | 1:100++ | + |
| | 28 | female | 44 | Houqi | + | − | − | − |
| | 29 | female | 44 | Liaoning | + | − | − | − |
| | 30 | female | 54 | Kequ | + | − | − | − |
| | 31 | female | 34 | Houqi | + | − | − | − |
| December 27 | 32 | male | 51 | Xing'an League | + | − | − | − |
| | 33 | female | 28 | Kequ | + | − | − | − |
| | 34 | female | 33 | Zhaqi | + | − | 1:200++ | + |
| | 35 | female | 54 | Liaoning | + | − | 1:100++ | + |
| | 36 | male | 21 | Liaoning | + | − | 1:200+++ | + |
| | 37 | male | 39 | Xing'an League | − | − | − | − |
| | 38 | male | 36 | Zuozhong | + | − | 1:200+++ | + |
| | 39 | male | 54 | Kequ | − | − | 1:25++ | + |
| | 40 | male | 48 | Zuozhong | + | − | 1:100++ | + |
| | 41 | male | 44 | Heilongjiang | + | + | 1:200+++ | + |
| | 42 | male | 54 | Jilin | + | + | − | − |
| | 43 | female | 31 | Zuozhong | + | + | 1:200++ | + |
| | 44 | female | 47 | Zuozhong | + | + | − | − |
| December 28 | 45 | female | 66 | Zuozhong | + | − | 1:50++ | + |
| | 46 | female | 38 | Zuozhong | + | − | 1:25++++ | + |
| | 47 | male | 26 | Chifeng | + | − | 1:50+++ | + |
| | 48 | female | 51 | Zhaqi | + | − | 1:100+ | + |
| | 49 | male | 39 | Xing'an League | + | − | 1:50+ | + |
| | 50 | male | 35 | Kequ | + | − | − | + |
| | 51 | male | 36 | Kequ | + | − | − | − |
| | 52 | male | 43 | Houqi | + | − | 1:50+ | + |
| January 5 | 53 | male | 43 | Houqi | + | − | 1:100++ | + |
| | 54 | male | 45 | Houqi | + | − | 1:100++ | + |
| | 55 | male | 23 | Houqi | + | − | 1:25++ | + |
| | 56 | male | 65 | Kequ | + | − | 1:25++++ | + |
| | 57 | male | 25 | Kailu | + | − | − | − |
| | 58 | male | 42 | Kailu | + | − | 1:25++ | + |
| | 59 | male | 31 | Zhaqi | + | − | 1:100++++ | + |
| | 60 | male | 31 | Zhaqi | + | − | − | − |
| | 61 | male | 57 | Zuozhong | + | − | 1:100++ | + |
| | 62 | female | 54 | Development District | + | − | 1:25+ | + |
| | 63 | male | 42 | Naiman | + | + | − | − |
| | 64 | male | 59 | Jilin | + | − | − | − |
| | 65 | male | 38 | Kailu | + | + | − | − |
| | 66 | female | 39 | Zuozhong | + | − | 1:25+ | + |
| | 67 | male | 39 | Houqi | + | − | − | − |
| | 68 | female | 41 | Xing'an League | + | − | − | − |
| | 69 | female | 66 | Kailu | + | − | − | − |
| May 22 | 70 | male | 30 | Development District | − | − | 1:25++ | + |

TABLE 2-continued

Test results of 300 cases

| Date | No. | Gender | Age | Address | PCR Blood Cells | PCR Serum | Clinic Result SAT | Clinic Result RBPT |
|---|---|---|---|---|---|---|---|---|
| | 71 | female | 27 | Houqi | − | + | − | − |
| | 72 | female | 32 | Development District | − | − | 1:25++ | + |
| | 73 | male | 38 | Jilin | − | − | 1:25++ | + |
| | 74 | male | 21 | Zuozhong | − | + | 1:200++++ | + |
| | 75 | male | 48 | Zuozhong | + | − | 1:50++ | + |
| | 76 | female | 26 | Kequ | − | + | − | − |
| | 77 | female | 53 | Houqi | + | − | 1:25++ | + |
| | 78 | male | 39 | Houqi | − | + | 1:50++ | + |
| | 79 | male | 42 | Kequ | + | + | 1:100+++ | + |
| | 80 | male | 26 | Zuozhong | + | − | 1:100++ | + |
| | 81 | male | 44 | Zuozhong | − | − | 1:25++ | + |
| | 82 | female | 44 | Kequ | + | + | 1:200+++ | + |
| | 83 | male | 29 | Zuozhong | − | + | − | − |
| | 84 | female | 30 | Kulun | − | − | 1:50+ | + |
| | 85 | male | 44 | Kequ | − | + | 1:50++ | + |
| | 86 | male | 42 | Kequ | + | + | 1:200++++ | + |
| | 87 | male | 30 | Zuozhong | + | − | 1:100++ | + |
| | 88 | male | 47 | Liaoning | + | − | 1:100++ | + |
| | 89 | male | 35 | Development District | + | − | 1:100+++ | + |
| | 90 | male | 42 | Xing'an League | + | + | 1:50+++ | + |
| | 91 | male | 33 | Kequ | + | + | 1:200++++ | + |
| | 92 | male | 59 | Zhaqi | + | − | 1:200++++ | + |
| | 93 | female | 33 | Development District | − | + | 1:50++ | + |
| | 94 | male | 42 | Liaoning | − | + | 1:25+++ | + |
| | 95 | male | 36 | Zuozhong | + | + | 1:200+++ | + |
| | 96 | female | 57 | Kequ | + | − | − | − |
| | 97 | male | 49 | Houqi | + | + | 1:200+++ | + |
| | 98 | male | 51 | Zuozhong | + | + | 1:50+++ | + |
| | 99 | male | 58 | Zuozhong | + | − | 1:200++ | + |
| | 100 | male | 43 | Kequ | + | − | 1:100+++ | + |
| | 101 | female | 41 | Zuozhong | − | − | 1:25++ | + |
| | 102 | male | 48 | Zhaqi | + | + | 1:200++ | + |
| | 103 | male | 52 | Liaoning | + | + | 1:200+++ | + |
| | 104 | female | 46 | Zuozhong | + | + | 1:200++++ | + |
| | 105 | female | 57 | Houqi | + | − | − | − |
| | 106 | female | 34 | Kequ | − | − | 1:25++ | + |
| | 107 | male | 56 | Kequ | − | + | 1:50+++ | + |
| | 108 | male | 47 | Jilin | + | + | 1:200++++ | + |
| | 109 | male | 51 | Zuozhong | + | + | 1:200+++ | + |
| | 110 | male | 51 | Houqi | + | − | − | − |
| | 111 | male | 51 | Hebei | + | + | 1:100++ | + |
| | 112 | female | 44 | Zuozhong | − | + | 1:50++ | + |
| | 113 | female | 53 | Kequ | + | − | − | − |
| | 114 | male | 45 | Zuozhong | + | − | 1:100++ | + |
| | 115 | female | 64 | Zuozhong | + | − | 1:200++ | + |
| | 116 | male | 60 | Kequ | − | − | 1:50+ | + |
| May 23 | 117 | male | 47 | Zuozhong | + | + | 1:50++ | + |
| | 118 | female | 48 | Kequ | + | + | 1:200++++ | + |
| | 119 | male | 56 | Kequ | + | + | 1:200++++ | + |
| | 120 | male | 28 | Houqi | − | + | − | − |
| | 121 | female | 54 | Kequ | + | + | 1:100+ | + |
| | 122 | male | 43 | Xing'an League | + | − | 1:200+++ | + |
| | 123 | male | 53 | Xing'an League | + | − | 1:200++ | + |
| | 124 | female | 52 | Houqi | − | + | − | − |
| | 125 | male | 68 | Zuozhong | − | + | − | − |
| | 126 | male | 41 | Kequ | − | + | 1:50++ | + |
| | 127 | male | 37 | Kequ | − | + | 1:100+ | + |
| | 128 | male | 24 | Kequ | + | + | 1:200++++ | + |
| | 129 | male | 27 | Heilongjiang | + | + | 1:50+ | + |
| | 130 | male | 24 | Kailu | + | + | 1:100+ | + |
| | 131 | male | 31 | Houqi | + | + | 1:200++++ | + |
| | 132 | female | 50 | Heilongjiang | + | − | − | − |
| | 133 | male | 37 | Heilongjiang | − | + | − | − |
| | 134 | male | 49 | Houqi | − | + | 1:100++ | + |
| | 135 | male | 29 | Houqi | + | + | 1:200++ | + |
| | 136 | female | 28 | Kequ | − | + | − | − |
| | 137 | male | 45 | Houqi | − | + | 1:50+++ | + |

TABLE 2-continued

Test results of 300 cases

| Date | No. | Gender | Age | Address | PCR Blood Cells | PCR Serum | Clinic Result SAT | Clinic Result RBPT |
|---|---|---|---|---|---|---|---|---|
| | 138 | male | 51 | Development District | − | − | 1:50+ | + |
| | 139 | male | 26 | Kequ | − | + | 1:100++ | + |
| | 140 | male | 33 | Zuozhong | + | + | 1:200++ | + |
| | 141 | male | 44 | Zuozhong | − | − | − | + |
| | 142 | female | 40 | Zuozhong | + | − | − | − |
| | 143 | female | 44 | Zuozhong | + | − | 1:200++ | + |
| | 144 | male | 47 | Development District | + | − | 1:100+++ | + |
| | 145 | male | 37 | Liaoning | − | − | 1:50+ | + |
| | 146 | female | 26 | Heilongjiang | − | + | − | − |
| | 147 | male | 58 | Development District | + | + | 1:200++++ | + |
| | 148 | male | 29 | Liaoning | + | + | 1:200++ | + |
| | 149 | male | 30 | Kequ | + | + | 1:200++ | + |
| | 150 | male | 5 | Heilongjiang | − | − | 1:25++++ | + |
| | 151 | male | 41 | Kequ | + | − | 1:200++ | + |
| | 152 | male | 29 | Zuozhong | − | + | 1:100++ | + |
| | 153 | female | 38 | Kailu | − | − | 1:25++ | + |
| | 154 | male | 54 | Kequ | + | − | 1:100+++ | + |
| | 155 | male | 43 | Zuozhong | + | − | 1:100+++ | + |
| | 156 | male | 42 | Zuozhong | + | + | 1:200++++ | + |
| | 157 | female | 33 | Houqi | + | − | − | − |
| | 158 | female | 49 | Houqi | + | − | − | − |
| | 159 | male | 33 | Houqi | + | − | 1:100++ | + |
| | 160 | male | 58 | Zuozhong | − | + | 1:50++ | + |
| | 161 | male | 42 | Houqi | − | − | 1:25++ | + |
| | 162 | male | 55 | Development District | + | + | 1:50+++ | + |
| | 163 | male | 31 | Houqi | − | + | 1:50++ | + |
| | 164 | male | 44 | Houqi | + | + | 1:200++++ | + |
| | 165 | male | 54 | Houqi | + | + | 1:200++ | + |
| | 166 | female | 30 | Zuozhong | − | + | − | − |
| | 167 | male | 32 | Kequ | + | − | − | − |
| | 168 | male | 33 | Liaoning | + | + | 1:200++++ | + |
| | 169 | female | 60 | Youzhong | + | − | − | − |
| | 170 | male | 57 | Liaoning | + | + | 1:200+++ | + |
| | 171 | male | 57 | Kulun | + | + | 1:100+++ | + |
| | 172 | male | 41 | Zhaqi | + | − | 1:200+++ | + |
| | 173 | male | 27 | Liaoning | + | + | 1:50++ | + |
| | 174 | male | 21 | Chifeng | + | + | 1:50++ | + |
| | 175 | male | 28 | Houqi | − | − | 1:25++ | + |
| | 176 | male | 47 | Liaoning | + | − | − | − |
| | 177 | male | 40 | Kequ | + | − | − | − |
| | 178 | male | 31 | Development District | + | + | 1:100++ | + |
| | 179 | female | 45 | Houqi | + | + | 1:50++ | + |
| | 180 | male | 24 | Houqi | − | + | 1:200+++ | + |
| | 181 | male | 53 | Houqi | + | + | 1:25++ | + |
| | 182 | female | 43 | Xing'an League | + | − | − | − |
| | 183 | male | 34 | Liaoning | + | + | 1:50++ | + |
| | 184 | male | 34 | Development District | + | + | 1:50++ | + |
| May 24 | 185 | male | 43 | Kequ | + | − | − | − |
| | 186 | male | 20 | Zuozhong | − | + | 1:200++ | + |
| | 187 | female | 54 | Zhaqi | + | − | − | − |
| | 188 | male | 39 | Zuozhong | + | − | 1:200++++ | + |
| | 189 | female | 42 | Xing'an League | + | + | 1:200++++ | + |
| | 190 | male | 50 | Kequ | − | + | 1:100++ | + |
| | 191 | female | 56 | Liaoning | + | − | − | − |
| | 192 | female | 36 | Liaoning | | + | 1:25++ | + |
| | 193 | male | 60 | Zuozhong | + | + | 1:50++ | + |
| | 194 | female | 59 | Kequ | + | + | 1:200+++ | + |
| | 195 | male | 64 | Xing'an League | + | + | 1:200++++ | + |
| | 196 | male | 37 | Zuozhong | − | + | 1:100+++ | + |
| | 197 | female | 27 | Zuozhong | − | + | 1:25++ | + |
| | 198 | male | 24 | Zhaqi | + | − | 1:200++++ | + |
| | 199 | female | 50 | Kailu | + | − | 1:200+++ | + |
| | 200 | male | 22 | Kequ | − | + | − | − |
| | 201 | male | 29 | Zuozhong | + | − | 1:25++ | + |
| | 202 | male | 11 | Kailu | + | + | 1:200++++ | + |

TABLE 2-continued

Test results of 300 cases

| Date | No. | Gender | Age | Address | PCR Blood Cells | PCR Serum | Clinic Result SAT | Clinic Result RBPT |
|---|---|---|---|---|---|---|---|---|
| | 203 | male | 59 | Zuozhong | + | + | 1:100++ | + |
| | 204 | female | 40 | Heilongjiang | + | − | − | − |
| | 205 | male | 62 | Houqi | + | + | 1:200++++ | + |
| | 206 | female | 46 | Kequ | + | + | 1:200+++ | + |
| | 207 | male | 37 | Jilin | + | − | 1:25++ | + |
| | 208 | female | 31 | Zuozhong | − | + | − | − |
| | 209 | male | 40 | Houqi | + | + | 1:200++++ | + |
| | 210 | male | 61 | Zhaqi | + | + | 1:200++++ | + |
| | 211 | female | 57 | Zuozhong | + | − | − | − |
| | 212 | male | 33 | Zuozhong | + | − | 1:25++ | + |
| | 213 | female | 45 | Shandong | + | + | 1:200+++ | + |
| | 214 | male | 40 | Houqi | + | + | 1:200++ | + |
| | 215 | female | 44 | Kulun | − | + | 1:50++ | + |
| | 216 | male | 26 | Zuozhong | − | + | 1:25++ | + |
| | 217 | male | 50 | Chifeng | + | − | − | − |
| | 218 | male | 29 | Kailu | + | + | 1:200+++ | + |
| | 219 | male | 24 | Liaoning | − | + | 1:200++ | + |
| | 220 | male | 37 | Zhaqi | + | − | 1:25++ | + |
| | 221 | female | 40 | Xing'an League | + | − | − | − |
| | 222 | male | 44 | Kequ | + | + | 1:100++ | + |
| | 223 | female | 71 | Kequ | + | − | − | − |
| | 224 | male | 55 | Houqi | + | − | 1:25++ | + |
| | 225 | male | 31 | Kailu | + | + | 1:200++++ | + |
| | 226 | female | 61 | Liaoning | + | + | 1:50++ | + |
| | 227 | male | 61 | Zhaqi | + | + | 1:100++ | + |
| | 228 | female | 45 | Houqi | + | − | − | − |
| | 229 | male | 46 | Houqi | + | − | − | − |
| | 230 | male | 32 | Kailu | − | + | 1:100++ | + |
| | 231 | female | 24 | Zuozhong | + | + | 1:100++ | + |
| | 232 | male | 30 | Zuozhong | + | + | 1:200++ | + |
| May 25 | 233 | female | 40 | Houqi | − | + | 1:25++ | + |
| | 234 | female | 32 | Kequ | + | − | − | − |
| | 235 | male | 31 | Kequ | + | + | 1:50++ | + |
| | 236 | female | 49 | Kailu | + | − | − | − |
| | 237 | male | 30 | Zuozhong | + | + | 1:200+++ | + |
| | 238 | female | 29 | Naiman | + | + | 1:50++ | + |
| | 239 | female | 50 | Kailu | + | − | − | − |
| | 240 | male | 37 | Zuozhong | − | + | 1:25++ | + |
| | 241 | male | 45 | Kequ | + | + | 1:200++++ | + |
| | 242 | female | 28 | Kequ | + | + | 1:200+++ | + |
| | 243 | male | 57 | Development District | + | − | − | − |
| | 244 | female | 26 | Naiman | − | + | 1:25+++ | + |
| | 245 | female | 36 | Zuozhong | + | + | 1:200+++ | + |
| | 246 | male | 57 | Zuozhong | + | − | 1:50++ | + |
| | 247 | male | 27 | Chifeng | − | + | 1:200+++ | + |
| | 248 | female | 43 | Jilin | − | + | − | − |
| | 249 | male | 31 | Xilinhot | + | + | 1:200+++ | + |
| | 250 | male | 45 | Liaoning | + | + | 1:100++ | + |
| | 251 | female | 39 | Kailu | + | − | − | − |
| | 252 | male | 54 | Heilongjiang | + | − | 1:200++++ | + |
| | 253 | male | 56 | Kequ | + | + | 1:200++++ | + |
| | 254 | male | 39 | Zuozhong | + | − | − | − |
| | 255 | male | 38 | Houqi | + | − | 1:25++ | − |
| | 256 | female | 50 | Houqi | + | + | 1:50++ | + |
| | 257 | male | 33 | Zuozhong | − | + | 1:25+ | + |
| | 258 | male | 54 | Xing'an League | + | − | − | − |
| | 259 | female | 55 | Kequ | + | + | 1:200++++ | + |
| | 260 | male | 32 | Zuozhong | + | + | 1:200++ | + |
| | 261 | male | 43 | Kequ | + | − | 1:25+ | + |
| | 262 | male | 68 | Zuozhong | + | − | 1:200+ | + |
| | 263 | female | 34 | Xing'an League | − | + | − | − |
| | 264 | male | 26 | Kailu | − | + | 1:200++++ | + |
| | 265 | male | 44 | Zuozhong | + | + | 1:200++++ | + |
| | 266 | male | 51 | Zuozhong | + | − | 1:50++ | + |
| | 267 | female | 49 | Kequ | + | − | 1:25+ | + |
| | 268 | female | 51 | Zuozhong | + | − | − | − |
| | 269 | male | 30 | Zuozhong | + | + | 1:100++ | + |
| | 270 | male | 48 | Houqi | + | − | 1:50++ | + |
| | 271 | male | 75 | Kailu | − | + | 1:200++ | + |

TABLE 2-continued

Test results of 300 cases

| Date | No. | Gender | Age | Address | PCR Blood Cells | PCR Serum | Clinic Result SAT | Clinic Result RBPT |
|---|---|---|---|---|---|---|---|---|
| May 26 | 272 | male | 50 | Naiman | + | − | − | − |
| | 273 | male | 40 | Naiman | − | + | 1:50+ | + |
| | 274 | male | 45 | Houqi | + | − | 1:200++ | + |
| | 275 | female | 61 | Zhaqi | + | − | − | − |
| | 276 | male | 37 | Zhaqi | − | + | − | − |
| | 277 | male | 42 | Houqi | − | + | 1:100++ | + |
| | 278 | female | 55 | Kequ | + | + | 1:100++++ | + |
| | 279 | male | 45 | Development District | + | + | 1:100+ | + |
| | 280 | female | 40 | Zuozhong | − | − | − | + |
| | 281 | female | 54 | Zuozhong | − | − | 1:25+ | + |
| | 282 | male | 40 | Houqi | − | + | 1:200++ | + |
| | 283 | male | 60 | Zhaqi | + | + | 1:200++++ | + |
| | 284 | male | 26 | Zhaqi | + | + | 1:200+++ | + |
| | 285 | male | 25 | Houqi | + | + | 1:200++++ | + |
| | 286 | female | 51 | Naiman | + | − | 1:25+ | + |
| | 287 | male | 35 | Naiman | − | + | − | − |
| | 288 | male | 65 | Kequ | + | + | 1:100++ | + |
| | 289 | male | 56 | Kequ | + | + | 1:200+++ | + |
| | 290 | male | 59 | Kailu | + | − | − | − |
| | 291 | male | 36 | Kequ | + | − | 1:50+ | + |
| | 292 | female | 38 | Zuozhong | + | + | 1:50++ | + |
| | 293 | male | 29 | Houqi | + | + | 1:200++++ | + |
| | 294 | male | 56 | Development District | + | + | 1:100+++ | + |
| | 295 | male | 51 | Liaoning | + | + | 1:100+ | + |
| | 296 | female | 59 | Youqi | + | + | 1:200+++ | + |
| | 297 | male | 37 | Youqi | + | + | 1:200++++ | + |
| | 298 | female | 23 | Xing'an League | − | + | 1:200++++ | + |
| | 299 | male | 63 | Kequ | + | + | 1:100+ | + |
| | 300 | male | 47 | Zhaqi | + | + | 1:50++ | + |

The invention claimed is:

1. A pretreatment kit for detecting *Brucella* infection, comprising Solution I, Solution II, Solution III, Solution IV, and Solution V,
   wherein Solution I is an aqueous solution containing 368 mg/42 mL of sodium chloride;
   Solution II is an aqueous solution containing 1 g/125 mL of sodium chloride, 25 mg/125 mL of potassium chloride, 177.5 mg/125 mL of disodium hydrogen phosphate and 33.75 mg/125 mL of potassium dihydrogen phosphate;
   Solution III is an aqueous solution containing 42.399 mg/35 mL of trihydroxymethyl aminomethane, 306.81 mg/35 mL of sodium chloride and 102.284 mg/35 mL of ethylenediamine tetraacetic acid;

Solution IV is 2-[4-(2,4,4-trimethylpentan-2-yl)phenoxy]ethanol or an aqueous solution containing 35 mg/0.35 mL of sodium dodecyl sulfate; and Solution V is double distilled water.

2. A method for detecting or diagnosing *Brucella* infection of a subject, comprising:
    isolating and extracting DNA from a sample containing living cells using the pretreatment kit of claim 1;
    detecting whether a *Brucella* DNA is present in the extracted DNA; and
    diagnosing as having the *Brucella* infection when the *Brucella* DNA is present in the extracted DNA.

3. The method according to claim 2, further comprising enriching the living cells, wherein the sample is a peripheral blood.

4. The method according to claim 2, wherein the living cells are blood cells.

5. The method according to claim 2, further comprising detecting whether the *Brucella* DNA is in a body fluid or the living cells of the sample.

6. The method according to claim 2, wherein the method detects *Mycobacterium tuberculosis* infection or other intracellular parasitic infection.

7. The method according to claim 5,
    wherein the body fluid is serum, and the living cells are blood cells, and
    the serum and the living cells are from a peripheral blood taken from the subject.

8. The method according to claim 7, wherein the blood cells are living monocytes in the peripheral blood.

9. The method according to claim 2, wherein isolating and extracting the *Brucella* DNA comprises:
    taking 0.2 mL of serum into a 1.5 mL Ep tube;
    centrifuging at room temperature, 15000×g for 15 minutes to obtain a first pellet and a first supernatant; discarding the first supernatant;
    adding 0.2 mL of Solution V to the 1.5 mL Ep tube; shaking; centrifuging at room temperature, 15000×g for 10 minutes to obtain a second pellet and a second supernatant; discarding the second supernatant;
    adding 20 μL of Solution V to the 1.5 mL Ep tube; shaking, and instantaneously centrifuging;
    heating at 100° C. for 10 minutes; placing in ice or in a −20° C. refrigerator for 2 minutes; centrifuging at room temperature, 15000×g for 10 seconds to obtain a third supernatant; and
    sucking 15 or 10 μL of the third supernatant as a template for PCR.

10. The method according to claim 2, wherein isolating and extracting the *Brucella* DNA comprises:
    taking 1 mL of peripheral blood into a tube; adding 1 mL of Solution I into the tube and mixing uniformly to obtain a mixture; spreading the mixture in wells of a cell culture plate, and then incubating at 37° C. for 1 hour to obtain a sediment and a blood supernatant; discarding the blood supernatant in the wells, and washing the wells with Solution II until there is no red color;
    adding 1 mL of Solution II to the wells of the cell culture plate, repeatedly blowing, and transferring the sediment including living monocytes at the bottom of the wells to a 1.5 mL Ep tube;
    centrifuging the Ep tube at 4° C., 500×g for 5 minutes to obtain a first pellet and a first supernatant; discarding the first supernatant;
    adding 800 μL of Solution III to the first pellet, and mixing thoroughly;
    adding 8 μL of Solution IV, and mixing thoroughly; incubating at 55° C. for 1 hour;
    centrifuging the Ep tube at room temperature, 8000 rpm for 10 minutes to obtain a second pellet and a second supernatant; discarding the second supernatant;
    adding 800 μL of Solution V, and mixing thoroughly; centrifuging at room temperature, 8000 rpm for 10 minutes to obtain a third pellet and a third supernatant; discarding the third supernatant;
    adding 20 μL of Solution V, shaking, and mixing thoroughly; heating at 100° C. for 10 minutes;
    centrifuging at room temperature, 15000×g for 10 seconds to obtain a fourth supernatant; and
    sucking 15 or 10 μL of the fourth supernatant as a template for PCR.

11. The method according to claim 9, wherein the PCR is fluorescent quantitative PCR.

12. The method according to claim 10, wherein the PCR is fluorescent quantitative PCR.

* * * * *